United States Patent
Hu (10) Patent No.: US 11,802,818 B2
(45) Date of Patent: Oct. 31, 2023

(54) SYSTEM AND METHOD FOR MONITORING FOR THE PRESENCE OF ELEMENTS

(71) Applicant: Computational International LLC, Newark, DE (US)

(72) Inventor: Ken Pingsheng Hu, Newark, DE (US)

(73) Assignee: COMPUTATIONAL INTERNATIONAL LLC, Newark, DE (US)

( * ) Notice: Subject to any disclaimer, the term of this patent is extended or adjusted under 35 U.S.C. 154(b) by 69 days.

(21) Appl. No.: 17/478,014

(22) Filed: Sep. 17, 2021

(65) Prior Publication Data

US 2022/0082478 A1  Mar. 17, 2022

Related U.S. Application Data

(60) Provisional application No. 63/079,939, filed on Sep. 17, 2020.

(51) Int. Cl.
*G01N 1/24* (2006.01)
*G01N 33/00* (2006.01)

(52) U.S. Cl.
CPC ........... *G01N 1/24* (2013.01); *G01N 33/0009* (2013.01); *G01N 33/0011* (2013.01); *G01N 33/0016* (2013.01); *G01N 33/0031* (2013.01)

(58) Field of Classification Search
CPC ...................................................... G01N 1/24
USPC ............................................. 73/23.2, 863.71
See application file for complete search history.

(56) References Cited

U.S. PATENT DOCUMENTS

| | | | | |
|---|---|---|---|---|
| 5,345,810 A | * | 9/1994 | Rosen | .................... G01N 25/56 73/29.02 |
| 7,360,461 B2 | * | 4/2008 | Desrochers | .............. G01N 1/26 73/864.81 |
| 9,651,531 B2 | * | 5/2017 | Desrochers | .............. F24F 11/36 |
| 11,067,558 B2 | * | 7/2021 | Chou | ................. G01N 33/0075 |
| 2004/0005715 A1 | | 1/2004 | Schabron | |
| 2006/0060004 A1 | * | 3/2006 | Desrochers | .............. G01N 1/22 73/863.71 |

(Continued)

FOREIGN PATENT DOCUMENTS

| | | | | |
|---|---|---|---|---|
| CN | 101248345 A | * | 8/2008 | ............... G01N 1/22 |
| CN | 101248345 B | | 2/2013 | |

(Continued)

OTHER PUBLICATIONS

Ibrahim A. Turman, Riyad J. Hroush, Majdi Zalloum, Design and Building of Gas Analyzer, College Of Engineering & Technology Mechanical Engineering Departments Graduation Project, Hebron-Palestine, May 2013, p. 96.*

(Continued)

*Primary Examiner* — Stephanie E Bloss
*Assistant Examiner* — Kevin C Butler
(74) *Attorney, Agent, or Firm* — BAKER & MCKENZIE LLP (57) ABSTRACT

A testing system is provided that includes a plurality of valves and a plurality of pumps. At least one of the pumps is coupled to at least one of the valves. A plurality of sensor arrays are coupled to at least one of the pumps or at least one of the valves for detecting at least one element. Each of the sensor arrays includes at least one serial connected sensor or parallel connected sensor.

20 Claims, 6 Drawing Sheets

(56) References Cited

U.S. PATENT DOCUMENTS

| | | | |
|---|---|---|---|
| 2009/0028208 A1* | 1/2009 | Martin | G01N 1/405 374/45 |
| 2015/0153299 A1* | 6/2015 | Chou | G01N 33/0075 204/406 |
| 2019/0137467 A1* | 5/2019 | Chou | G01N 33/0032 |
| 2021/0041411 A1* | 2/2021 | Hu | G01N 30/20 |
| 2022/0042953 A1* | 2/2022 | Hu | G01N 30/12 |
| 2022/0082478 A1* | 3/2022 | Hu | G01N 1/2273 |

FOREIGN PATENT DOCUMENTS

| | | | | |
|---|---|---|---|---|
| CN | 104680878 A | * | 6/2015 | G09B 9/00 |
| CN | 104680878 B | | 9/2017 | |
| CN | 207472887 U | * | 6/2018 | |
| CN | 207472887 U | | 6/2018 | |
| CN | 207689474 U | * | 8/2018 | |
| CN | 207689474 U | | 8/2018 | |
| JP | 2005-291715 A | | 10/2005 | |
| JP | 2005291715 A | * | 10/2005 | G01N 33/0031 |
| JP | 2007-071635 A | | 3/2007 | |
| JP | 2007071635 A | * | 3/2007 | |
| WO | WO-03050511 A1 | * | 6/2003 | G01N 27/626 |
| WO | WO-2006135575 A1 | * | 12/2006 | G01N 1/22 |
| WO | WO-2022061085 A1 | * | 3/2022 | G01N 1/24 |

OTHER PUBLICATIONS

Chia Jung Lu et al., Chamber evaluation of a portable GC with tunable retention and microsensor-array detection for indoor air quality monitoring, Journal of Environmental Monitoring, 2006, 8, 270-278 (Year: 2006).*

Naoki Kakita et al., MEMS Based Microstructure Array Design and Its Quantitative Analysis of Micropreconcentrator for Cancer Biomarker Diagnosis, IEEE, 2013, p. 4 (Year: 2013).*

G.G. Mandayo et al., System To Control Indoor Air Quality in Energy Efficient Buildings, Science Direct (https:/www.elsevier.com/locate/uclim), Urban Climate 14 (2015) 475-485 (Year: 2015).*

An International Search Report and Written Opinion dated Jan. 18, 2022 in connection with International application No. PCT/US2021/050832.

* cited by examiner

SYSTEM AND METHOD FOR MONITORING FOR THE PRESENCE OF ELEMENTS

CROSS REFERENCE TO RELATED APPLICATIONS

This application claims priority to U.S. provisional application No. 63/079,939 filed on Sep. 17, 2020, the contents of which is included herein in its entirety.

BACKGROUND

Volatile organic compounds (VOCs) include both human-made and naturally occurring chemical compounds. Many scents and odors are the results of VOCs. However, many VOCs are dangerous to human health or can cause harm to the environment. More specifically, although harmful VOCs are not often acutely toxic, they typically compound long-term adverse health effects. Advanced knowledge, such as by regularly occurring measurements, of the presence of VOCs is an essential matter for public health and safety. VOCs are also emitted from living organisms or subjects, including but not limited to humans. They can be used as an indicator or a biomarker to determine the state of these living subjects, including but not limited to the health thereof.

The measurement for the presence of elements typically requires large devices, such as on the order of at least 2'×2'×2', which are very expensive due, in part, to their size and complexity. These devices usually use one type of sensor or multiple of the same type of sensors. Moreover, such large measurement devices generally employ specific or singular modality methods such as chromatography, which historically has necessitated temperature and moisture controlled clean rooms, and the use of expensive consumable gases as well as specialist training equivalent to a Ph.D. degree. The foregoing severely limits the broad availability of testing elements of interest for health screening or environmental monitoring and space exploration. These limitations are exacerbated in the developing world or disadvantaged communities due to the lack of funds for these prior art devices or nearby laboratories to transport infrastructure or supplies for testing in such prior art devices.

Alternative methods for testing these elements are generally quite expensive, suffer from inferior accuracy, provide infrequent measurement windows, or require specialized expertise for operation and maintenance. No available technologies provide accurate, inexpensive element testing with broad availability at a low cost.

Current element detection devices, like VOC detection devices, rely on sensors limited by types and modality and therefore limit element detection capabilities. For example, for VOC testing, Gas Chromatography (GC) types of VOC detection devices use photoionization detector (PID) sensors to identify and separate VOCs. These sensors are slow and expensive. Other sensors such as micro-electromechanical systems (MEMS), gold nanoparticle-based MEMS chips, transistors, or carbon nano-tube-based MEMS are fast and lower cost. However, these sensors cannot perform sufficient VOC identification or separation, and sometimes these MEMS sensors cannot identify individual VOCs.

BRIEF SUMMARY

According to one aspect of the subject matter described in this disclosure, a testing system is provided. The testing system includes a plurality of valves and a plurality of pumps. At least one of the pumps is coupled to at least one of the valves. A plurality of sensor arrays are coupled to at least one of the pumps or at least one of the valves for detecting at least one element. Each of the sensor arrays includes at least one serial connected sensor or parallel connected sensor.

According to one aspect of the subject matter described in this disclosure, a method of analyzing a gas mixture is provided. The method includes directing a sample into one of a plurality of valves. Also, the method includes detecting one or more elements in the sample using a plurality of sensor arrays. The sensor arrays are coupled to at least one pump or at least one valve. Each of the sensor arrays includes at least one serial connected sensor or parallel connected sensor.

According to one aspect of the subject matter described in this disclosure, a sensor is provided. The sensor includes a plurality of first connectors where at least one of the first connectors is coupled to at least one first outlet. Also, the sensor includes a plurality of second connectors where at least one of the second connectors is coupled to a second outlet. Moreover, the sensor includes a plurality of sensing elements for sensing at least one element. Each of the sensing elements are coupled to at least one first connector and at least one second connector. The sensing elements, the first connectors, and the second connectors are arranged to form a serial connected sensor or a parallel connected sensor.

Additional features and advantages of the disclosure are described in, and will be apparent from, the detailed description of this disclosure.

BRIEF DESCRIPTION OF THE DRAWINGS

The disclosure is illustrated by way of example, and not by way of limitation, in the figures of the accompanying drawings in which like reference numerals are used to refer to similar elements. It is emphasized that various features may not be drawn to scale and the dimensions of various features may be arbitrarily increased or reduced for clarity of discussion.

DETAILED DESCRIPTION

The figures and descriptions provided herein may have been simplified to illustrate aspects that are relevant for a clear understanding of the herein described devices, systems, and methods, while eliminating, for the purpose of clarity, other aspects that may be found in typical similar devices, systems, and methods. Those of ordinary skill may recognize that other elements and/or operations may be desirable and/or necessary to implement the devices, systems, and methods described herein. But because such elements and operations are well known in the art, and because they do not facilitate a better understanding of the present disclosure, a discussion of such elements and operations may not be provided herein. However, the present disclosure is deemed to inherently include all such elements, variations, and modifications to the described aspects that would be known to those of ordinary skill in the art.

The terminology used herein is for the purpose of describing particular example embodiments only and is not intended to be limiting. For example, as used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Although the terms first, second, third, etc., may be used herein to describe various elements, components, regions, layers and/or sections, these elements, components, regions, layers and/or sections should not be limited by these terms. These terms may be only used to distinguish one element, component, region, layer or section from another element, component, region, layer or section. That is, terms such as "first," "second," and other numerical terms, when used herein, do not imply a sequence or order unless clearly indicated by the context.

The disclosure includes a system and method for monitoring, identifying, and quantifying elements. The elements may include organic and inorganic compounds, such as volatile organic compounds (VOCs) or other carbon-based inorganic compounds, in gas environments. More particularly, the disclosure relates to a smaller, cost effective system that concentrates, identifies, and quantifies the elements. Existing systems are large in footprint and highly complex, and are thus very expensive, in contrast to the disclosed embodiments.

Figure 1:
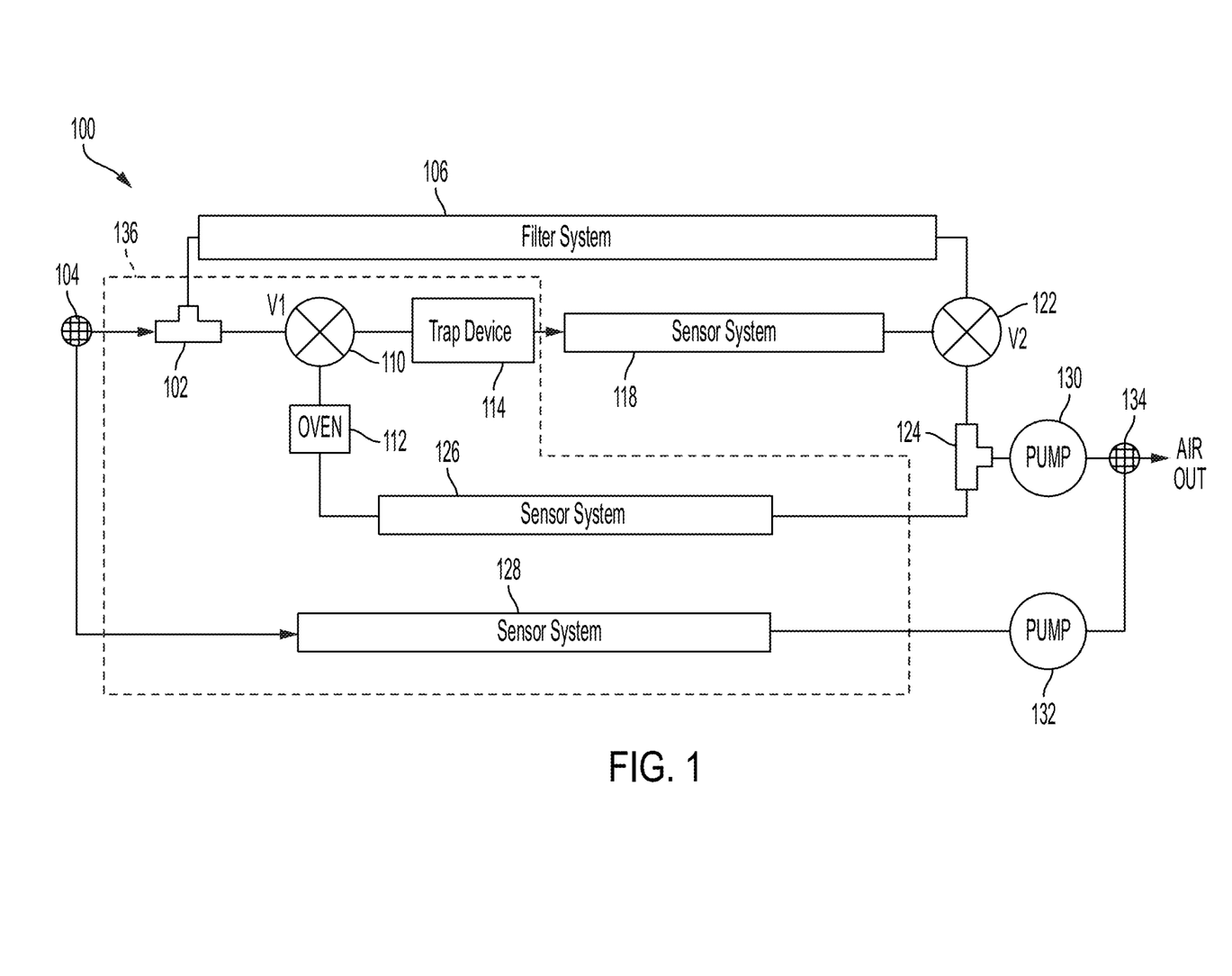
FIG. 1 is a schematic diagram illustrating an exemplary embodiment of a testing system for element analysis, in accordance with some embodiments.

FIG. 1 is a schematic diagram illustrating an exemplary embodiment of a testing system 100 for element analysis, in accordance with some embodiments. In particular, FIG. 1 shows testing system 100 having a tee 102 that receives at its input a sample of gas and/or air through an inlet 104 of an enclosing testing system 136. The tee 102 is connected to a filter system 106 and a control valve 110. Control valve 110 may receive a voltage V1 for valve control. Control valve 110 is also connected to an oven 112 and a Trap device 114. Trap device 114 is used to collect volatiles received at its input, and is connected to a first sensor system 118.

Filter system 106 may perform selective filtering without removing key elements, such as VOCs or other inorganic compounds, and may filter water from its input. Moreover, filter system 106 may control its airflow using constriction. Control valve 122 is connected to filter system 106, first sensor system 118, and tee 124. Control valve 122 may receive a voltage V2 for valve control. First sensor system 118 may be used to measure the pressures and temperatures at one end of Trap device 114.

Oven 112 is connected to a second sensor system 126 for testing purposes. The second sensor system 126 is connected to tee 124. A third sensor system 128 receives the sample of gas and/or air at one input and is connected to a pump 132. The tee 124 is connected to a pump 130. Pumps 130 and 132 are connected to an outlet 134 for removal from testing system 100.

Testing system 100 includes a testing section 136 defining the section within testing system 100 that performs the various testing analysis, such as gas chromatography (GC) VOC and/or total volatile organic compound (TVOC) analysis. Testing section 136 may comprise tee 102, control valve 110, oven 112, Trap device 114, and second and third sensor systems 126 and 128. The second sensor system 126 may be used for GC VOC testing while third sensor system 128 is used for TVOC testing. Note non-VOC testing may be performed by the second sensor system 126 and the third sensor system 128 as well. In some embodiments, testing section 136 may include other arrangements of components besides those shown in FIG. 1 to be described hereinafter. Testing section 136 is coupled to both enclosure inlet 104 and enclosure outlet 134.

In some implementations, the first sensor system 118, the second sensor system 126, and the third sensor system 128 may each include at least one sensor. In some implementations, each of the first sensor system 118, the second sensor system 126, and the third sensor system 128 may include a sensor array. In some implementations, the sensor array may include serial connected sensors or parallel connected sensors to be discussed further hereinafter.

In some implementations, testing system 100 may include a plurality of different connections between its numerous components than those shown in FIG. 1 and still accomplish the operations described herein. In addition, tees 102 and 124 may provide inlet ports that remain continuously open or may be manually or automatically closed. Trap device 114 may be capable of reversibly adsorbing a chemical compound, and in particular an organic compound, or more specifically a VOC.

In some embodiments, the testing system 100 may include elements used in gas chromatography (GC) in combination with MEMS sensors, PID sensors, mass spectrometry, high-field asymmetric-waveform ion-mobility spectrometry (FAIMS), or RF-DC ion-mobility spectrometry.

In some embodiments, the first sensor system 118, the second sensor system 128, and the third sensor system 128 may include one or more sensor arrays for detection, identification, separation, or measurement of elements including but not limited to electrons, atoms, subatomic elements, partials such as quarks, inorganic compounds, or organic compounds.

In some embodiments, the first sensor system 118, the second sensor system 128, and the third sensor system 128 may include sensor arrays for detection, identification, separation, or measurement of gravitational fields, electromagnetic fields, phases of matter such as gas, liquid, solid, or other exotic forms. In some embodiments, the first sensor system 118, the second sensor system 126, and the third sensor system 128 may include sensor arrays for volatile organic compound (VOC) testing or total volatile organic compound (TVOC) testing.

In some embodiments, the enclosure inlet 104 includes a tee or the like. In some embodiments, the enclosure outlet 134 includes a tee or the like.

In some embodiments, the filter system 106 may include a charcoal filter. The charcoal filter may be formed of activated charcoal. Heaters used by Trap device 114 and oven 112 may be any suitable heater. Coolers used for cooling Trap device 114 and oven 112 may be any suitable cooler. Pumps 130 and 132 may be any suitable pump capable of generating partial vacuum for operating the system.

In some cases, enclosure inlet 104 for the testing system 100 may be one or more ports going to both of the aforementioned analysis channels. Likewise, the enclosure outlet 134 from the analysis channels may comprise one or more ports from the enclosure.

In some embodiments, the system pressures may be preferably between 0 and 1 atmosphere. In some embodiments, the connections between the enclosure inlet 104 and the Trap device 114 may contain PEEK or stainless steel, and most preferably may comprise passivated stainless-steel. Other connections may use stainless steel, PEEK, FEP tubing or FEP-lined tubing.

In some implementations, the connections between the Trap device 114 and the oven 112 may contain only stainless steel.

In some embodiments, oven 112 may use one or more "cold spots" that are designed into oven 112 so as to be sufficiently long to achieve cryofocusing. The exact length may depend on the cooling mechanism used, the type of column, the thermal mass of the oven, and other factors known to the skilled artisan.

In some embodiments, heating may be achieved with low-voltage DC powered cartridge heater(s)—each of which may require a heating controller. Heating control may be capable of increasing the oven temperature at a linear rate. Oven 112 may include cartridge heater element(s) that may be controlled by a continuously variable DC voltage.

In some embodiments, the temperature of oven 112 may be controlled by heating and cooling. This temperature may be measured and controlled (via heating and cooling) in a refined manner.

In some embodiments, the temperature of Trap device 114 may likewise be controlled with heating and cooling. This temperature may be measured and controlled (via heating and cooling) in a refined manner.

The temperature of Trap device 114 may range from −10 deg C. to 220 deg C.

In some instances, insulation may be used to protect the connections between Trap device 114 and the oven 112. If the insulation is unable to maintain the required temperatures, it may be necessary to include heating with low-voltage DC or AC powered cartridge heater(s).

Of course, the skilled artisan will appreciate the prospective need for additional circuits and controls in light of the instant disclosure. By way of example, additional controls may be included for refined control of specific heating and cooling circuits.

In some embodiments, the second and third sensor systems 126 and 128 may be subjected to temperatures from −40 deg C. to +100 deg C. This is much less than the Trap device 114 and oven 112 temperature ranges, and thus it may be necessary to thermally insulate a sensor system from the Trap device 114 and oven heating zones.

In some implementations, the second and third sensor systems 126 and 128 may operate in temperatures between −40 deg C. to +100 deg C. In this case, the second and third sensor systems 126 and 128 can be maintained in the desired temperature range, and there need not be any active heating or cooling of the second and third sensor systems 126 and 128. However, if the desired temperature range cannot be maintained, then heating or cooling may be required.

In some embodiments, relative humidity, temperature, pressure, and voltage may be monitored at a sensor.

In some embodiments, testing system 100 may include additional pumps besides pumps 130 and 132. A single output voltage may control each of the pumps in testing system 100.

In some embodiments, testing system 100 may include additional control valves besides control valves 110 and 122. A single output voltage may control each of the control valves in testing system 100.

In some embodiments, a diagnostic port may allow an external device or screen to be used to display running status information. This diagnostic port may be RS232 or the like.

In some implementations, the data from the testing system 100 may be transmitted remotely for data capture and analysis. Data transmission may be modular, and may allow for any known transmission method, such as Bluetooth, WiFi, 4G, or the like. If data transmission halts or fails, the data can be buffered inside testing system 100, and transmitted upon restoration of the communications link. The testing system 100 may be controlled remotely.

In some instances, testing system 100 may include a real-time clock (RTC) that provides the time at which data is captured. In some embodiments, the initialization of the RTC may be done through a diagnostic port or via the time-stamp provided through a 4G transmission link or the like.

In some embodiments, a separate pressure sensor may be located inside each of the sensor enclosures of the second and third sensor system 126 and 128. A separate pressure sensor may be located on a controller board (in an open position) so that the current atmospheric conditions of testing system 100 can be captured.

In some embodiments, a separate humidity/temperature sensor may be located inside each of the second and third sensor system 126 and 128. A separate humidity/temperature sensor may be located on a controller board (in an open position) so that the current atmospheric conditions of the testing system 100 can be captured.

In some implementations, the enclosure for the testing system 100 may be either plastic, aluminum, stainless steel, copper, fiber glass or the like in order to keep weight down and enhance portability. The system enclosure may provide protection against dust ingress and some water resistance or waterproofing. An inlet fan can be used to draw gas and/or air into the system, such as through a baffle which prevents water ingress and which provides finger guard protection, and passes through the enclosure inlet. An outlet fan can be used to draw gas and/or air out of the system, such as through a baffle which prevents water ingress and which provides finger guard protection, and out the enclosure outlet.

In some embodiments, the system may readily operate in various ambient temperatures and conditions, including varying humidity levels, altitudes, and atmospheric temperatures. The system may also vary as to the required power supply, such as based on numbers of elements selected as discussed above.

Figure 2:
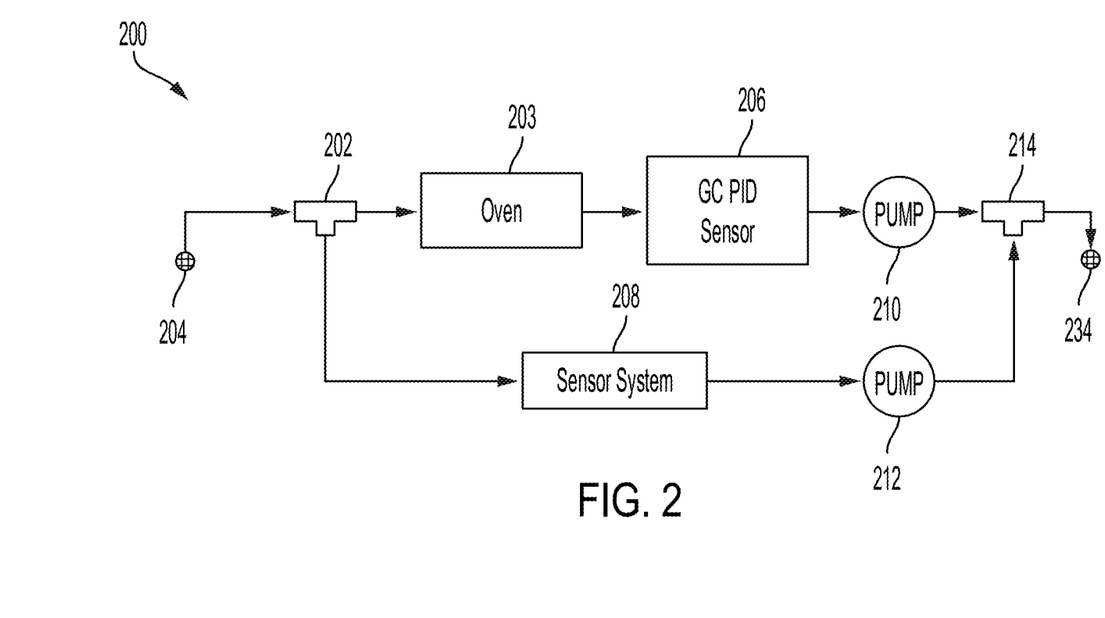
FIG. 2 is a schematic diagram illustrating an exemplary embodiment of a testing section used in conjunction with a testing system, in accordance with some embodiments.

FIG. 2 is a schematic illustrating an exemplary embodiment of a testing section 200 used in conjunction with a testing system, in accordance with some embodiments. Testing section 200 receives a sample of gas and/or air from enclosure inlet 204. Tee 202 receives the gas and/or air from enclosure inlet 204. Tee 202 is connected to an oven 203 and a sensor system 208. Oven 203 is connected to a GC PID sensor 206. GC PID sensor 206 is connected to a pump 210, and sensor system 208 is connected to a pump 212. Pumps 210 and 212 are connected to a tee 214. Tee 214 directs the exhaust from the GC PID sensor 206 and sensor system 208 out to enclosure outlet 234. The properties of the components of testing section 200 are similar to the properties of the components of testing section 136 of FIG. 1.

In some implementations, the sensor system 208 may include at least one sensor. In some implementations, the sensor system 208 may include a sensor array. In some implementations, the sensor array may include serial connected sensors and/or parallel connected sensor, to be described further hereinafter.

In some embodiments, the testing section 200 may include elements used in gas chromatography (GC) in combination with MEMS sensors, PID sensors, mass spectrometry, high-field asymmetric-waveform ion-mobility spectrometry (FAIMS), or RF-DC ion-mobility spectrometry.

In some embodiments, the sensor system 208 may include sensor arrays for detection, identification, separation, or measurement of elements including but not limited to electrons, atoms, subatomic elements, partials such as quarks, inorganic compounds, or organic compounds. In some embodiments, the sensor system 208 may include sensor arrays for detection, identification, separation or measurement of gravitational fields, electromagnetic fields, phases of matter such as gas, liquid, solid, or other exotic forms. In some embodiments, the sensor system 208 may include sensor arrays for volatile organic compound (VOC) testing or total volatile organic compound (TVOC) testing.

Figure 3:
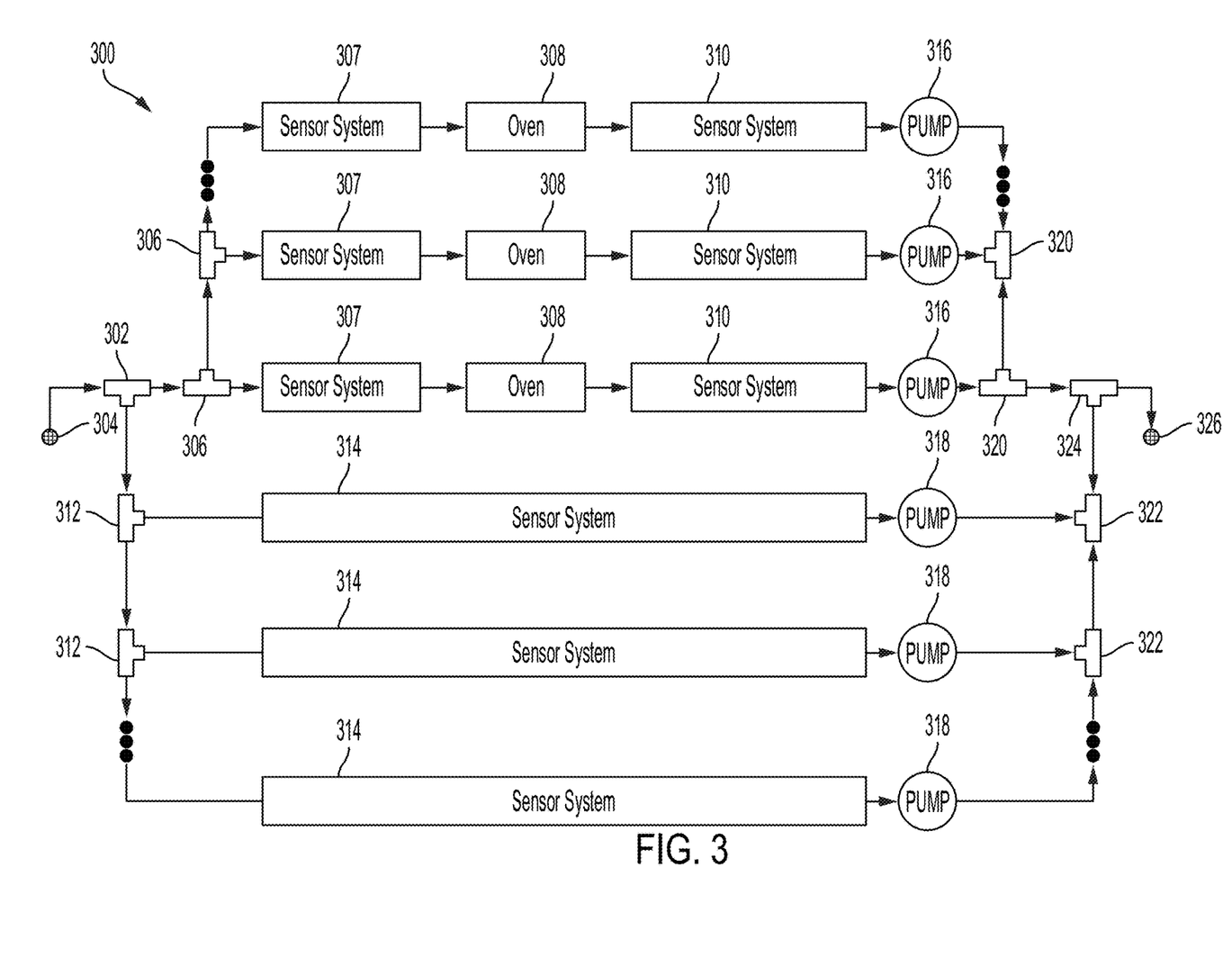
FIG. 3 is a schematic diagram illustrating an exemplary embodiment of a testing section used in conjunction with testing systems having sensor systems, in accordance with some embodiments.

FIG. 3 is a schematic diagram illustrating an exemplary embodiment of a testing section 300 used in conjunction with a testing system having sensor systems, in accordance with some embodiments. Testing section 300 can be used for performing multiple testing of elements. Testing section 300 includes a tee 302 that receives a sample of gas and/or air from enclosure inlet 304. Tee 302 is connected to one of a number of tees 306. Each of the tees 306 is connected to a corresponding different tee 306. Also, each of the tees 306 is connected to one of several first sensor systems 307. Each of the first sensor systems 307 is connected to one of several ovens 308. Each of the ovens 308 is connected to a different second sensor system of multiple second sensor systems 310. Each of the second sensor systems 310 is connected to one of several pumps 316. Each of the pumps 316 is connected to one of several tees 320. Moreover, each of the tees 320 is connected to a corresponding different tee 320. One of the tees 320 is connected to enclosure tee 324.

Tee 302 is also connected to one of a number of tees 312. Each of the tees 312 is connected to a corresponding different tee 312. Also, each of the tees 312 are connected to one of a number of third sensor systems 314. Each of the third sensor systems 314 is connected to one of many pumps 318. In addition, each of the pumps 318 is connected to one of several tees 322. Each of the tees 322 is connected to a corresponding different tee 322. One of the tees 322 is connected to enclosure tee 324. Enclosure tee 324 is used to direct the exhaust produced by second sensor systems 310 and third sensor systems 314 to enclosure outlet 326. The properties of the components of testing section 300 is similar to the properties of similar components of testing section 136 of FIG. 1.

In some implementations, the first sensor system 307, the second sensor system 310, and the third sensor system 314 may each include at least one sensor. In some implementations, each of the first sensor system 307, the second sensor system 310, and the third sensor system 314 may include a sensor array. In some implementations, the sensor array may include serial connected sensors and/or parallel connected sensors to be described further hereinafter.

In some embodiments, the testing section 300 may include elements used in gas chromatography (GC) in combination with MEMS sensors, PID sensors, mass spectrometry, high-field asymmetric-waveform ion-mobility spectrometry (FAIMS), or RF-DC ion-mobility spectrometry.

In some embodiments, the first sensor system 307, the second sensor system 310, and the third sensor system 314 may include sensor arrays for detection, identification, separation, or measurement of elements including but not limited to electrons, atoms, subatomic elements, partials such as quarks, inorganic chemical compounds, or organic chemical compounds. In some embodiments, the first sensor system 307, the second sensor system 310, and the third sensor system 314 may include sensor arrays for detection, identification, separation or measurement of gravitational fields, electromagnetic fields, phases of matter such as gas, liquid, solid, or other exotic forms. In some embodiments, the first sensor system 307, the second sensor system 310, and the third sensor system 314 may include sensor arrays for volatile organic compound (VOC) testing or total volatile organic compound (TVOC) testing.

Figure 4:
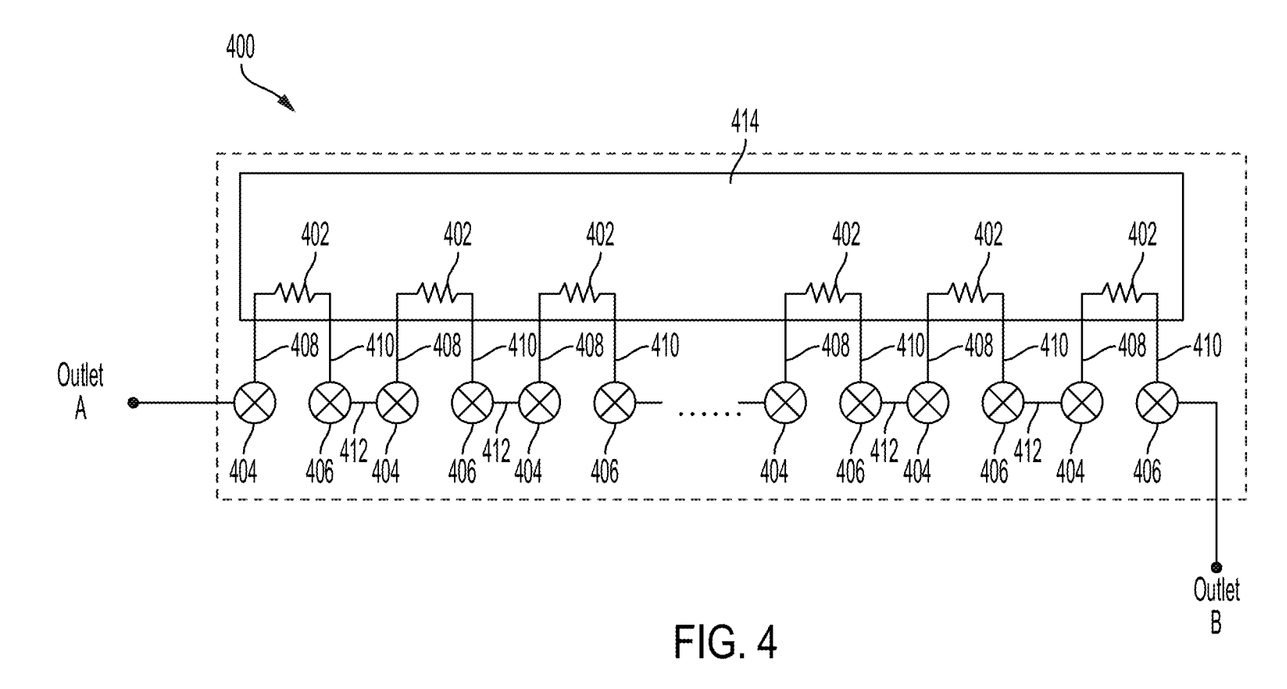
FIG. 4 is a schematic diagram illustrating a design of a serial connected sensor 400, in accordance with some embodiments.

FIG. 4 is a schematic diagram illustrating a design of a serial connected sensor 400, in accordance with some embodiments. The serial sensor 400 includes several sensing elements 402 serially arranged with several first connectors 404 and second connectors 406. In particular, each sensing element 402 is connected to a first connector 404 via wires 408 and a second connector 406 via wires 410. A certain number of first connectors 404 are connected to a certain number of second connectors 406 via wires 412. Outlet A is connected to one of the first connectors 404, and outlet B is connected to one of the second connectors 406. The sensing elements 402 may be formed on a substrate 414.

In some implementations, sensing element 402 may include dynamic resistors, micro-electromechanical systems (MEMS) structures, gold nano-particles, other metal and non-metal materials of a specific size and properties, carbon nanowires, graphene, or transistors.

In some embodiments, substrate 414 may include a silicon wafer, polymer, metal, or other natural or synthetic material(s).

In some implementations, connectors 404 and 406 may include bond-out pads or the like.

In some embodiments, connecting wires 408, 410, and 412 may include gold wires or the like.

Figure 5:
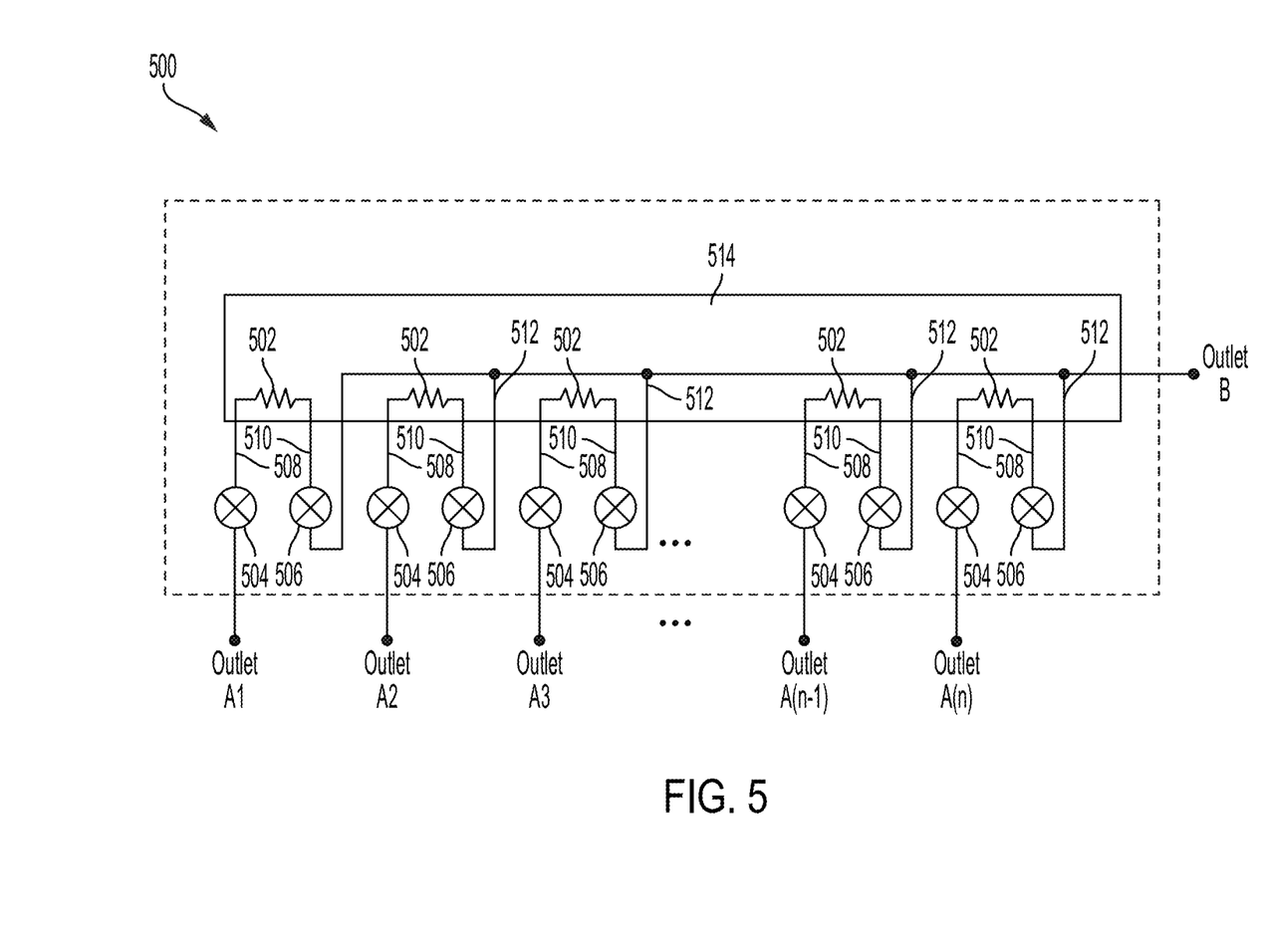
FIG. 5 is a schematic diagram illustrating a parallel connected sensor, in accordance with some embodiments.

FIG. 5 is a schematic diagram illustrating a parallel connected sensor 500, in accordance with some embodiments. The parallel connected sensor 500 includes several sensing elements 502 arranged in parallel with several first connectors 504 and second connectors 506. In particular, each sensing element 502 is connected to a first connector 504 via wires 508 and a second connector 506 via wires 510. Each first connector 504 is connected to one of the outlets Al—An. Each second connector 506 is connected to outlet B via wires 512. The sensing elements 502 may be formed on a substrate 514.

In some implementations, sensing element 502 may include dynamic resistors, micro-electromechanical systems (MEMS) structures, gold nano-particles, other metal and non-metal materials of a specific size and properties, carbon nanowires, graphene, or transistors.

In some embodiments, substrate 514 may include a silicon wafer, polymer, metal, or other natural or synthetic material(s).

In some implementations, connectors 504 and 506 may include bond-out pads or the like.

In some embodiments, connecting wires 508, 510, and 512 may include gold wires or the like.

Figure 6:
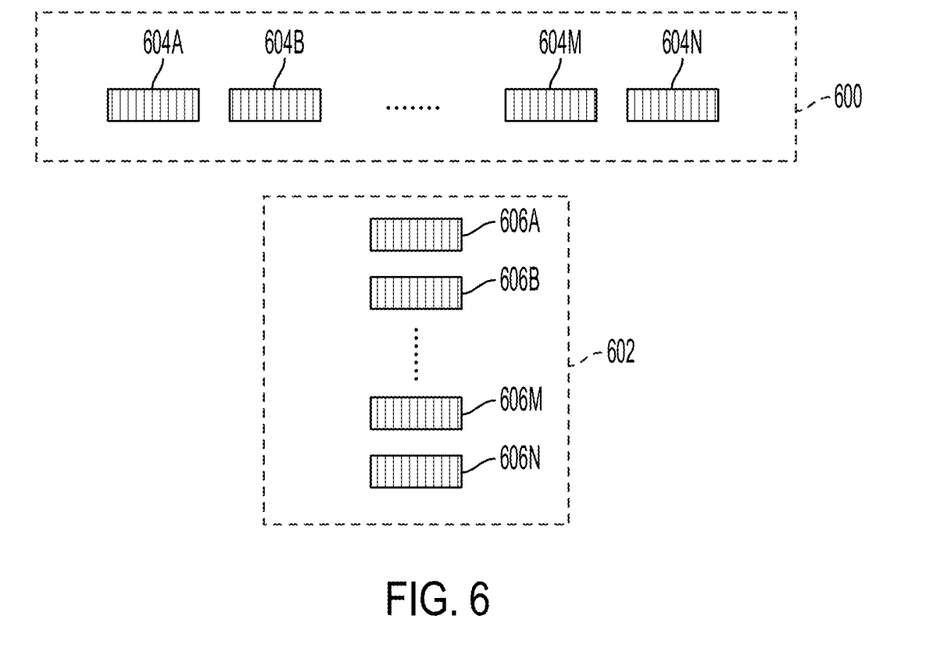
FIG. 6 is a schematic diagram illustrating two sensor arrays having a serial configuration and parallel configuration, in accordance with some embodiments.

FIG. 6 is a schematic diagram illustrating two sensor arrays 600 and 602 having a serial configuration and parallel configuration, in accordance with some embodiments. Sensor array 600 includes several sensors 604A-604N arranged serially. In some embodiments, the sensor array 600 may include a serial arrangement of sensors 606A-606N, where sensors 606A-606N are serial connected sensors as described in FIG. 4. In some embodiments, the sensor array 600 may include a serial arrangement of sensors 606A-606N, where sensors 606A-606N are parallel connected sensors as described in FIG. 5. In some embodiments, the sensor array 600 may include a serial arrangement of sensors 606A-606N, where sensors 606A-606N may include any combination of serial connected sensors, parallel connected sensors, and other sensor types, such as PID sensors, MEMS sensors, or the like.

Sensor array 602 includes several sensors 606A-606N arranged in parallel. In some embodiments, the sensor array 600 may include a parallel arrangement of sensors 606A-606N, where sensors 606A-606N are serial connected sensors similar to serial connected sensor 400 of FIG. 4. In some embodiments, the sensor array 602 may include a parallel arrangement of sensors 606A-606N, where sensors 606A-606N are parallel connected sensors similar to parallel connected sensor 500 of FIG. 5. In some embodiments, the sensor array 602 may include a parallel arrangement of sensors 606A-606N, where sensors 606A-606N may include any combination of serial connected sensors, parallel connected sensors, and other sensor types, such as PID sensors, MEMS sensors, or the like.

In some embodiments, the first sensor system 118, the second sensor system 128, and the third sensor system 128 of FIG. 1 may include sensor arrays 600 or 602.

In some embodiments, the sensor system 208 of FIG. 2 may include sensor arrays 600 or 602.

In some embodiments, the first sensor system 307, the second sensor system 310, and the third sensor system 314 of FIG. 3 may include sensor arrays 600 or 602.

The disclosure describes testing systems that may be used to provide measurements of elements identification, concentration, threat level, and so on. Such measurements may occur in a small footprint and without the need for other supporting reagents, carrier gas, such as Nitrogen, as is necessary in the solutions of the prior art. Also, the testing systems described herein may be used in space or another planet for identification, separation, or measurement of various elements.

Moreover, the disclosure describes testing systems that may provide stationary or portable indoor or outdoor environmental monitoring. Low-cost health screening as well as disease diagnostics or theranostics can be achieved using the testing systems described herein including screening for compounds that are toxic, carcinogenic, pollutants, or which contribute to the development of adverse environmental conditions. In addition, the testing systems described herein may provide portable or stationary testing capabilities for space exploration and other uses.

Reference in the specification to "one implementation" or "an implementation" means that a particular feature, structure, or characteristic described in connection with the implementation is included in at least one implementation of the disclosure. The appearances of the phrase "in one implementation," "in some implementations," "in one instance," "in some instances," "in one case," "in some cases," "in one embodiment," or "in some embodiments" in various places in the specification are not necessarily all referring to the same implementation or embodiment.

Finally, the above descriptions of the implementations of the present disclosure have been presented for the purposes of illustration and description. It is not intended to be exhaustive or to limit the present disclosure to the precise form disclosed. Many modifications and variations are possible in light of the above teaching. It is intended that the scope of the present disclosure be limited not by this detailed description, but rather by the claims of this application. As will be understood by those familiar with the art, the present disclosure may be embodied in other specific forms without departing from the spirit or essential characteristics thereof. Accordingly, the present disclosure is intended to be illustrative, but not limiting, of the scope of the present disclosure, which is set forth in the following claims.

What is claimed is:

1. A testing system, comprising:
    a plurality of valves;
    a plurality of pumps, at least one of the plurality of pumps being coupled to at least one of the plurality of valves; and
    a plurality of sensor arrays coupled to at least one of the plurality of pumps or at least one of the plurality of valves for detecting at least one element, wherein:
    a first sensor array comprised in the plurality of sensor arrays includes at least one serial connected sensor relative to an input and an output of the testing system,
    a second sensor array comprised in the plurality of sensor arrays includes one or more parallel connected sensors relative to the input and the output of the testing system,
    the at least one serial connected sensor is serially in fluidic communication with a first parallel sensor of the one or more parallel connected sensors, such that:
        the first parallel sensor is configured to detect a volatile organic compound (VOC) based on the fluidic communication between the at least one serial connected sensor and the first parallel sensor, and
        a second parallel sensor comprised in the one or more parallel sensors is configured to detect a total volatile organic compound (TVOC).

2. The testing system of claim 1, wherein the first sensor array comprises a serial arrangement of at least two serial connected sensors or a parallel arrangement of at least two parallel connected sensors.

3. The testing system of claim 1, wherein the second sensor array comprises a parallel arrangement of at least two serial connected and at least one parallel connected sensors.

4. The testing system of claim 1, wherein each of the plurality of sensor arrays comprises one or more sensors different from the least one serial connected sensor or the one or more parallel connected sensors.

5. The testing system of claim 1, further comprising an oven coupled to one of the plurality of valves and the first sensor array of the plurality of sensor arrays.

6. The testing system of claim 1, wherein the at least one element comprises electrons, atoms, subatomic elements, quarks, inorganic compounds, or organic compounds.

7. The testing system of claim 1, wherein the at least one element comprises gravitational fields, electromagnetic fields, or phases of matter, at least one sensor comprised in the plurality of sensor arrays being configured to measure or monitor one or more of pressure data, temperature data, humidity data, particle data, data mass data within the testing system.

8. A method of analyzing a gas mixture comprising:
directing a sample into one of a plurality of valves; and
detecting one or more elements in the sample using a plurality of sensor arrays, wherein:
the plurality of sensor arrays are coupled to at least one pump or at least one valve comprised in the plurality of valves,
a first sensor array comprised in the plurality of sensor arrays includes at least one serial connected sensor,
a second sensor array comprised in the plurality of sensor arrays includes one or more parallel connected sensors,
the at least one serial connected sensor is serially in fluidic communication with a first parallel sensor of the one or more parallel connected sensors, such that:
the first parallel sensor is configured to detect a volatile organic compound (VOC) based on the fluidic communication between the at least one serial connected sensor and the first parallel sensor, and
a second parallel sensor comprised in the one or more parallel sensors is configured to detect a total volatile organic compound (TVOC).

9. The method of claim 8, wherein detecting the one or more elements comprises utilizing a serial arrangement of at least two serial connected sensors or at least two parallel connected sensors comprised in the plurality of sensor arrays.

10. The method of claim 8, wherein detecting the one or more element comprises utilizing a parallel arrangement of at least two serial connected sensors or at least two parallel connected sensors comprised in the plurality of sensor arrays.

11. The method of claim 8, wherein detecting the one or more elements comprises utilizing one or more sensors different from the least one serial connected sensors or the one or more parallel connected sensors.

12. The method of claim 8, further comprising coupling an oven to one of the plurality of valves and the first sensor array of the plurality of sensor arrays.

13. The method of claim 8, wherein detecting the one or more elements comprises detecting electrons, atoms, subatomic elements, quarks, inorganic compounds, or organic compounds.

14. The method of claim 8, wherein detecting the one or more elements comprises detecting gravitational fields, electromagnetic fields, or phases of matter, at least one sensor comprised in the plurality of sensor arrays being configured to measure or monitor one or more of pressure data, temperature data, humidity data, particle data, data mass data.

15. A sensor, comprising:
a plurality of first connectors where at least one of the plurality of first connectors is coupled to at least one first outlet;
a plurality of second connectors where at least one of the plurality of second connectors is coupled to a second outlet;
a plurality of sensing elements for sensing at least one element, each of the plurality of sensing elements being coupled to at least one of the plurality of first connectors and at least one of the plurality of second connectors, wherein:
the sensing elements, the plurality of first connectors, and the plurality of second connectors are arranged to form one or more of a serial connected sensor or a parallel connected sensor,
the serial connected sensor is serially in fluidic communication with a first parallel sensor comprised in the plurality of sensing elements, such that:
the first parallel sensor is configured to detect a volatile organic compound (VOC) based on the fluidic communication between the serial connected sensor and the first parallel sensor, and
the parallel connected sensor is configured to detect a total volatile organic compound (TVOC).

16. The sensor of claim 15, wherein the serial connected sensor comprises one of the plurality of first connectors connected to one of the at least one first outlet and one of the plurality of second connectors is connected to the second outlet.

17. The sensor of claim 15, wherein the serial connected sensor comprises a select number of plurality of first connectors coupled to a select number of the plurality of second connectors.

18. The sensor of claim 15, wherein the at least one first outlet comprises a plurality of first outlets, and wherein the parallel connected sensor comprises each of the first connectors connected to at least one of the plurality of first outlets and each of the plurality of second connectors is connected to the second outlet.

19. The sensor of claim 15, wherein the parallel connected sensor comprises each of the first connectors coupled to one of a plurality of first outlets.

20. The sensor of claim 15, wherein the sensing elements comprise micro-electromechanical systems (MEMS), gold nano-particles, metal and non-metal materials, carbon nano wire, graphene, or transistors.

* * * * *